US012758731B2

(12) United States Patent
Tu et al.

(10) Patent No.: US 12,758,731 B2
(45) Date of Patent: Oct. 13, 2026

(54) DIAPHRAGM NASAL BREATHING REGULATOR

(71) Applicant: YUH & JIH INDUSTRIAL CO., LTD., Taichung City (TW)

(72) Inventors: Guo-Xian Tu, Taichung City (TW); I-Hsuan Tu, Taichung City (TW)

(73) Assignee: YUH & JIH INDUSTRIAL CO., LTD., Taichung City (TW)

( * ) Notice: Subject to any disclaimer, the term of this patent is extended or adjusted under 35 U.S.C. 154(b) by 385 days.

(21) Appl. No.: 18/630,183

(22) Filed: Apr. 9, 2024

(65) Prior Publication Data

US 2024/0366898 A1 Nov. 7, 2024

(30) Foreign Application Priority Data

May 4, 2023 (TW) ................................ 112116646

(51) Int. Cl.
*A61M 16/06* (2006.01)

(52) U.S. Cl.
CPC . *A61M 16/0666* (2013.01); *A61M 2210/0618* (2013.01)

(58) Field of Classification Search
CPC ....... A61M 16/0666–0677; A61M 15/08–085; A61M 25/02; A61M 2025/0226; A61M 2210/0618; A61M 29/00; A61F 5/08; A62B 23/06
See application file for complete search history.

(56) References Cited

U.S. PATENT DOCUMENTS

2007/0277832 A1* 12/2007 Doshi .................... A62B 23/06 128/207.18
2009/0194100 A1* 8/2009 Minagi .................... A61F 5/08 128/200.24
2011/0218451 A1* 9/2011 Lai ...................... A61M 15/085 600/533
2013/0081637 A1* 4/2013 Foley ...................... A61F 5/08 128/848
2016/0051397 A1* 2/2016 Nussbaum ............ A61M 15/08 128/848
2021/0137723 A1 5/2021 Kanwar

* cited by examiner

*Primary Examiner* — Rachel T Sippel
(74) *Attorney, Agent, or Firm* — Burris Law, PLLC

(57) ABSTRACT

A diaphragm nasal breathing regulator includes a cylinder, a diaphragm, and an engaging unit. The cylinder has a channel, two openings opposite to each other along an axial direction of the cylinder, and a bearing surface allowing the diaphragm to be disposed thereon. The engaging unit engages the diaphragm to the cylinder. The diaphragm is formed with a through hole, and is movable relative to the bearing surface between an inhaling position and an exhaling position. When the diaphragm is in the exhaling position, the diaphragm rests on the bearing surface, and air can flow only through the two openings, the channel, and the through hole. When the diaphragm is in the inhaling position, the diaphragm is away from the bearing surface in the axial direction, and air can flow through the two openings, the channel, the through hole, and a gap between the cylinder and the diaphragm.

12 Claims, 15 Drawing Sheets

DIAPHRAGM NASAL BREATHING REGULATOR

CROSS-REFERENCE TO RELATED APPLICATION

This application claims priority to Taiwanese Invention Patent Application No. 112116646, filed on May 4, 2023, the entire disclosure of which is incorporated by reference herein.

FIELD

The disclosure relates to a medical device for assisting breathing, and more particularly to a diaphragm nasal breathing regulator.

BACKGROUND

Referring to FIGS. 1 and 2, a conventional nasal breathing control apparatus 1 disclosed in U.S. Patent Application Publication No. US20210137723A1 is provided. The conventional nasal breathing control apparatus 1 includes two cylinders 11, a bridging portion 12 connected between the cylinders 11, and two floats 13 movably disposed in the cylinders 11, respectively. Each of the cylinders 11 has a chamber 111 and an extending projection 112. The chamber 111 has a first opening 113 that is on one end of the chamber 111, and a plurality of second openings 114 that are on an opposite end of the chamber 111, where a radius of each of the second openings 114 is smaller than that of the first opening 113. The extending projection 112 is disposed inside the chamber 111 and is adjacent to the first opening 113. Each of the floats 13 is disposed in the respective chamber 111 and is disposed between the second openings 114 and the extending projection 112.

The cylinders 11 are adapted to be inserted into two nostrils (not shown) of a user (not shown) with the first openings 113 facing away from the nostrils. As shown in FIG. 1, when the user is inhaling, for each of the cylinders 11, an upward airflow would impel the float 13 disposed in the chamber 111 of the cylinder 11 to move from the first opening 113 toward the second openings 114, and the upward airflow may pass around the float 13 and through the second openings 114. As shown in FIG. 2, when the user is exhaling, a downward airflow would impel the float 13 to move from the second openings 114 toward the first opening 113, and the float 13 would be blocked by the extending projection 112, thereby blocking the first opening 113.

As such, the conventional nasal breathing control apparatus 1 may train the user to inhale through their nostrils and exhale through their mouth. However, since the first opening 113 is blocked by the float 13, the downward airflow is unable to be released from the first opening 113 when the user attempts to exhale through their nostrils, causing discomfort similar to nasal congestion to the user, or even causing the user to have trouble breathing or be choked.

SUMMARY

Therefore, an object of the disclosure is to provide a diaphragm nasal breathing regulator that can alleviate at least one of the drawbacks of the prior art.

According to the disclosure, a diaphragm nasal breathing regulator includes a nasal plug. The nasal plug includes a cylinder, a diaphragm, and an engaging unit.

The cylinder surrounds and defines a channel that extends in an axial direction of the cylinder, that has a first opening and a second opening opposite to each other along the axial direction, and that includes a first channel section adjacent to the first opening and a second channel section adjacent to the second opening, where a radius of the second channel section is smaller than that of the first channel section. The cylinder includes a first inner surface that surrounds and defines the first channel section, a second inner surface that surrounds and defines the second channel section and that has an edge opposite to the second opening, and a bearing surface that is connected to the edge of the second inner surface and that faces the first opening.

The diaphragm is disposed in the first channel section and is formed with a through hole that extends through the diaphragm along the axial direction and that has a radius smaller than that of the second channel section. The diaphragm includes a first surface and a second surface that are opposite to each other along the axial direction and that face the first opening and the second opening respectively, an inner surrounding side that defines the through hole, and an outer surrounding side that is opposite to the inner surrounding side in a radial direction perpendicular to the axial direction.

The engaging unit includes a first engaging part that is formed on the first inner surface, and a second engaging part that is formed on the diaphragm and that movably engages the first engaging part in a manner where the diaphragm is movable relative to the bearing surface between an inhaling position and an exhaling position. When the diaphragm is in the exhaling position, the second surface of the diaphragm rests on the bearing surface, and air can flow only through the first opening, the first channel section, the through hole, the second channel section, and the second opening. When the diaphragm is in the inhaling position, the diaphragm is away from the bearing surface in the axial direction, and air can flow through the second opening, the second channel section, the through hole, the first channel section, a gap between the first inner surface and the outer surrounding side, and the first opening.

BRIEF DESCRIPTION OF THE DRAWINGS

Other features and advantages of the disclosure will become apparent in the following detailed description of the embodiment(s) with reference to the accompanying drawings. It is noted that various features may not be drawn to scale.

DETAILED DESCRIPTION

Figure 1:
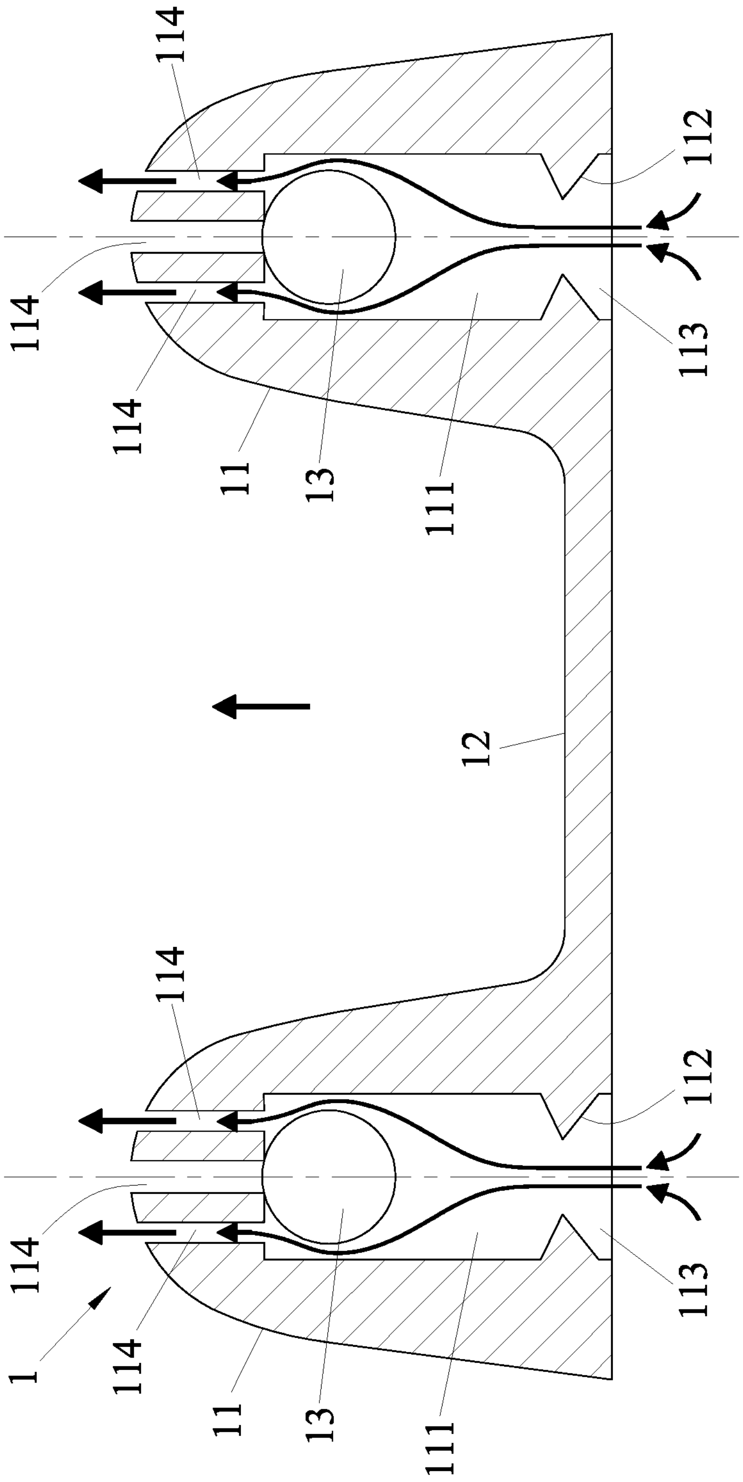
FIG. 1 PRIOR ART
FIG. 1 is a sectional view illustrating a conventional nasal breathing control apparatus disclosed in U.S. Patent Application Publication No. US20210137723A1, where a user using the conventional nasal breathing control apparatus is inhaling.
Figure 2:
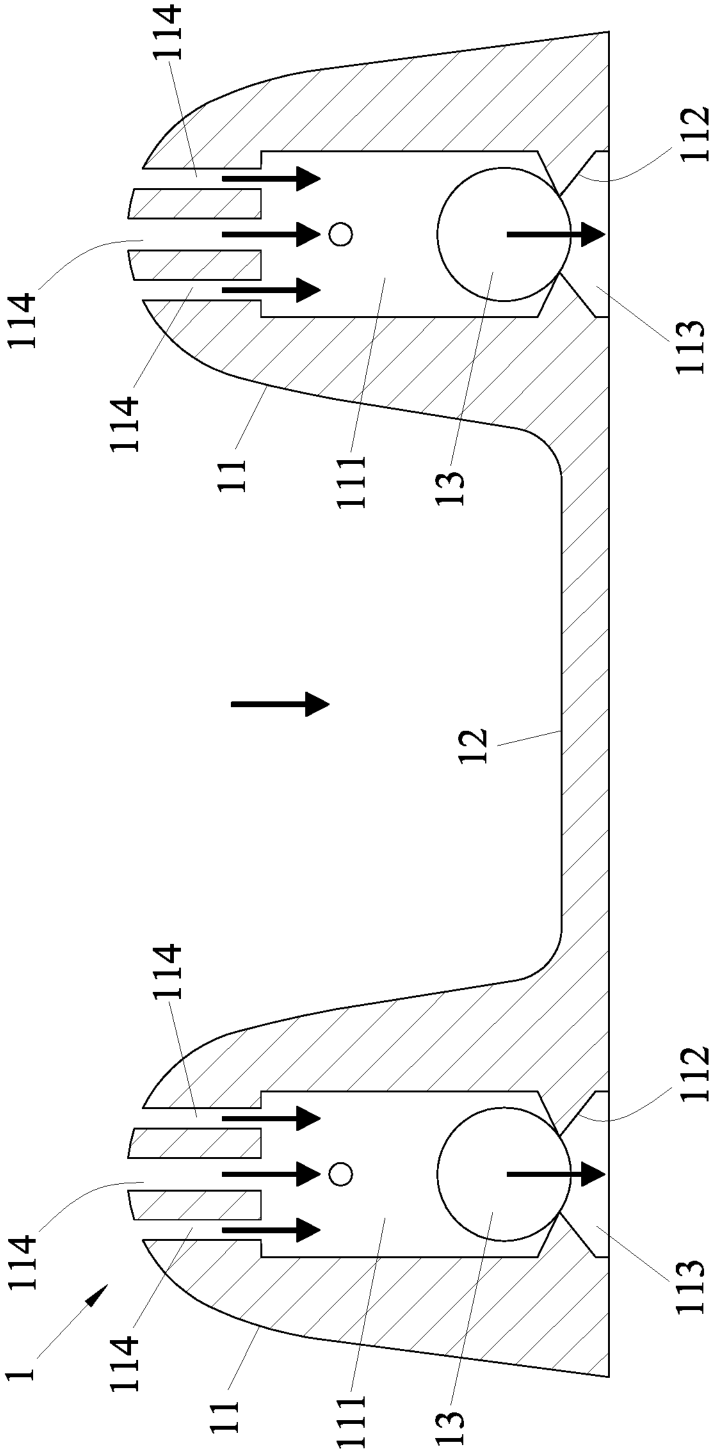
FIG. 2 PRIOR ART
FIG. 2 is another sectional view of the conventional nasal breathing control apparatus, where the user using the conventional nasal breathing control apparatus is exhaling.

Before the disclosure is described in greater detail, it should be noted that where considered appropriate, reference numerals or terminal portions of reference numerals have been repeated among the figures to indicate corresponding or analogous elements, which may optionally have similar characteristics.

It should be noted herein that for clarity of description, spatially relative terms such as "top," "bottom," "upper," "lower," "on," "above," "over," "downwardly," "upwardly" and the like may be used throughout the disclosure while making reference to the features as illustrated in the drawings. The features may be oriented differently (e.g., rotated 90 degrees or at other orientations) and the spatially relative terms used herein may be interpreted accordingly.

Figure 3:
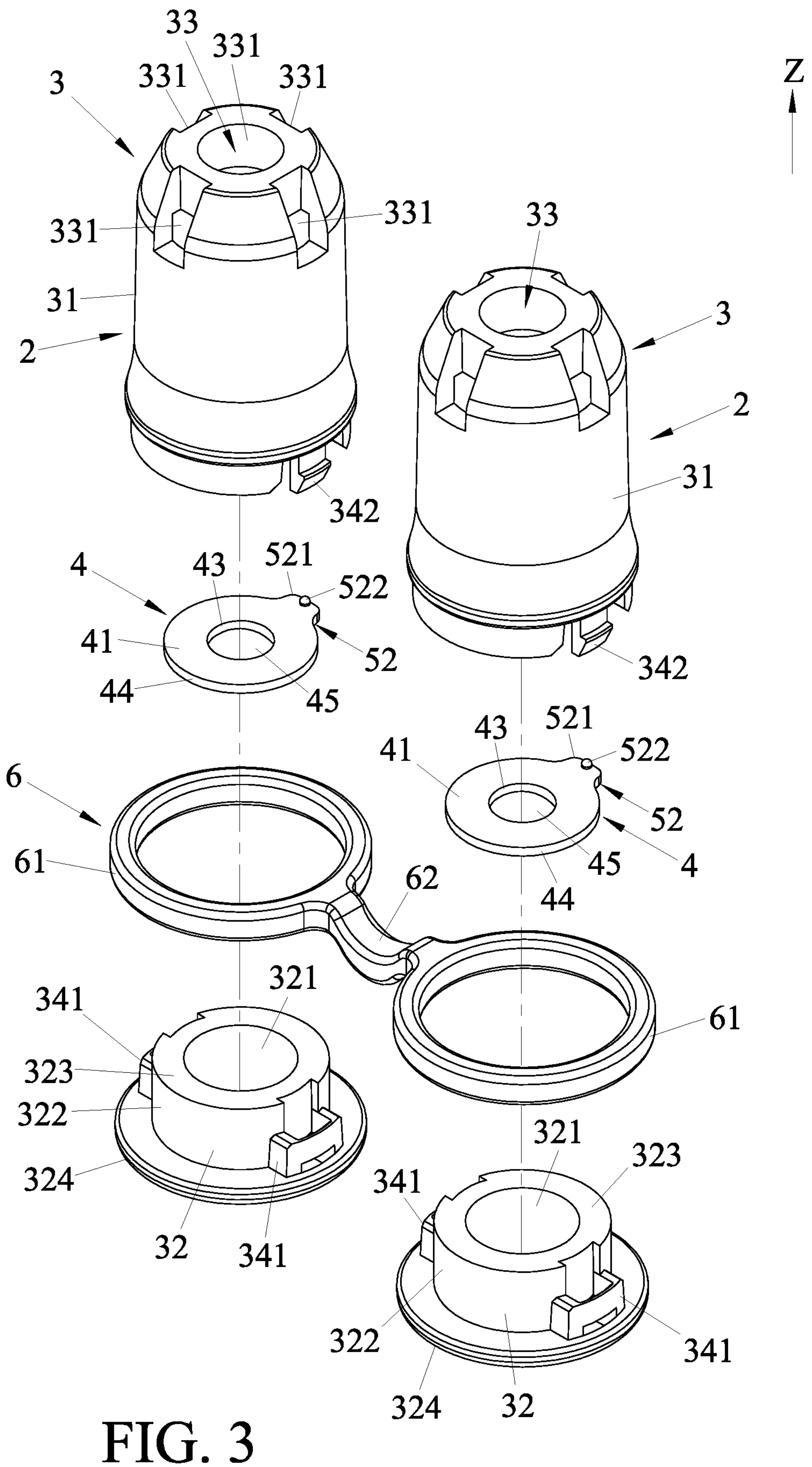
FIG. 3 is an exploded perspective view illustrating a diaphragm nasal breathing regulator according to a first embodiment of the disclosure.
Figure 4:
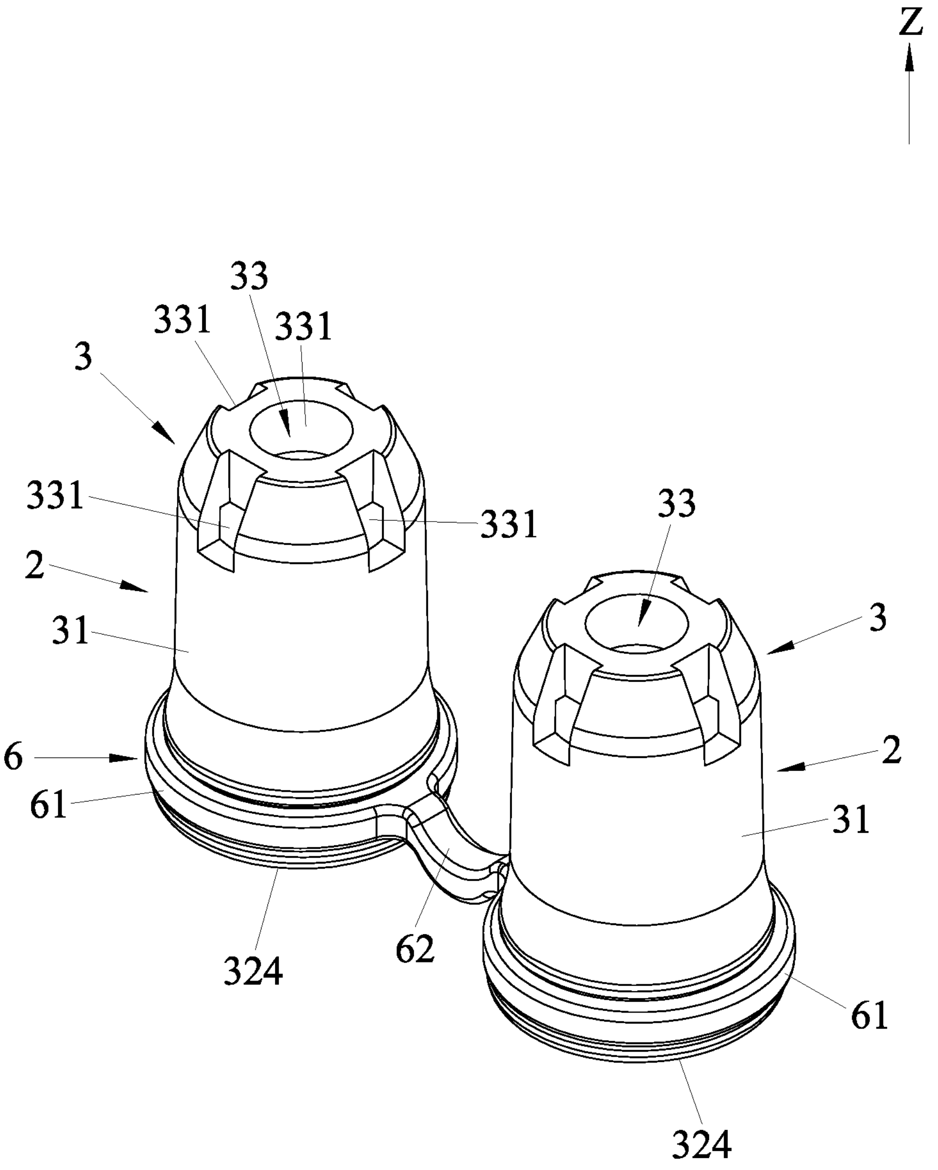
FIG. 4 is a perspective view illustrating the diaphragm nasal breathing regulator according to the first embodiment of the disclosure.
Figure 5:
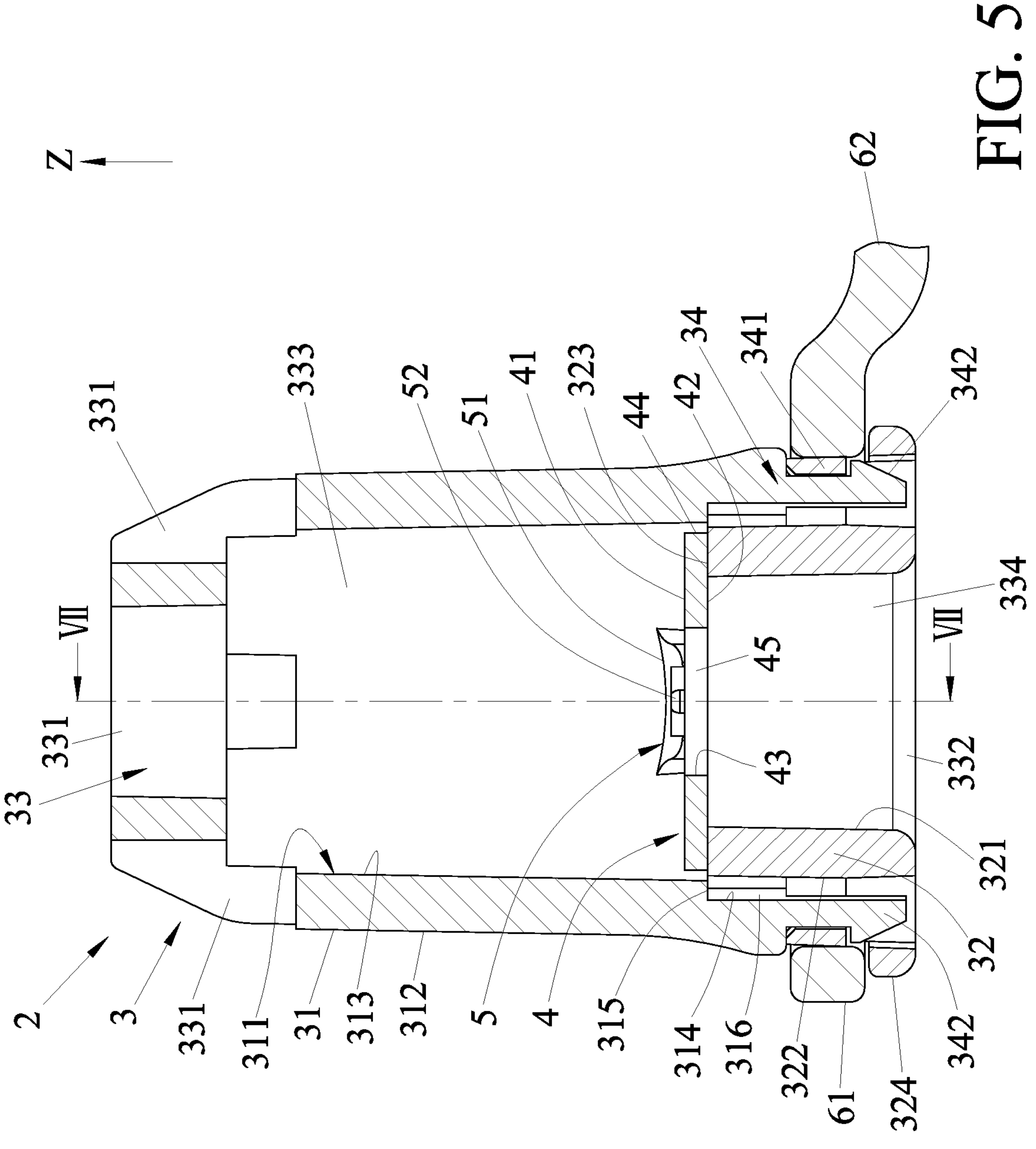
FIG. 5 is a fragmentary sectional view illustrating a nasal plug of the diaphragm nasal breathing regulator according to the first embodiment of the disclosure.
Figure 6:
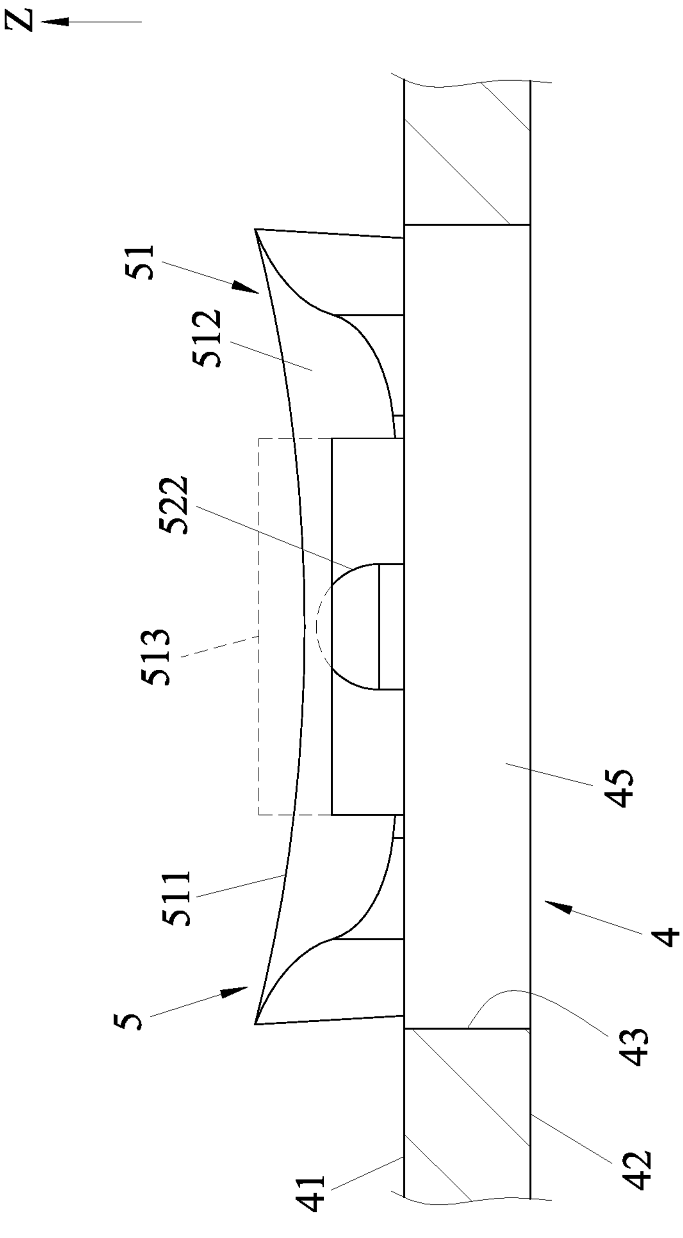
FIG. 6 is an enlarged fragmentary sectional view illustrating a portion of the diaphragm nasal breathing regulator shown in FIG. 5.

Referring to FIGS. 3 to 5, a diaphragm nasal breathing regulator according to a first embodiment of the disclosure includes two nasal plugs 2 and a connection component 6. Each of the nasal plugs 2 includes a cylinder 3, a diaphragm 4 and an engaging unit 5. Since the nasal plugs 2 are the same, only one of the nasal plugs 2 will be explained below.

The cylinder 3 includes an outer surrounding wall 31, an inner surrounding wall 32 that is surrounded by the outer surrounding wall 31 and that is detachably connected to the outer surrounding wall 31, a flange 324 that is connected to the inner surrounding wall 32, and an engaging mechanism 34 that interconnects the outer surrounding wall 31 and the inner surrounding wall 32.

The outer surrounding wall 31 and the inner surrounding wall 32 cooperatively surround and define a channel 33. The channel 33 extends in an axial direction (Z) of the cylinder 3, which is an up-down direction shown in FIG. 3, and has a plurality of first openings 331, and a second opening 332 opposite to the first openings 331 in the axial direction (Z), where the first openings 331 are located at the top of the channel 33 in the axial direction (Z) and the second opening 332 is located at the bottom of the channel 33. The channel 33 further includes a first channel section 333 that is adjacent to the first openings 331, and a second channel section 334 that is adjacent to the second opening 332, where a radius of the second channel section 334 is smaller than that of the first channel section 333.

In the first embodiment, there are five first openings 331, wherein four of the first openings 331 are spaced apart and arranged along a circumferential top edge of the outer surrounding wall 31, and surround the other one of the first openings 331. In some embodiments, the channel 33 may have only one first opening 331.

The outer surrounding wall 31 includes a first inner surface 311 and a first outer surface 312 that are opposite to each other in a radial direction which is perpendicular to the axial direction (Z). The first inner surface 311 includes a first surface portion 313 that is adjacent to the first openings 331 and that surrounds the first channel section 333, a second surface portion 314 that is adjacent to the second opening 332 (i.e., the second surface portion 314 is lower than the first surface portion 313 in the axial direction (Z)), and a shouldering surface portion 315 that is connected to and between the first surface portion 313 and the second surface portion 314. Specifically, the shouldering surface portion 315 is connected between a bottom edge of the first surface portion 313 and a top edge of the second surface portion 314, and faces downward in the axial direction (Z). The second surface portion 314 surrounds and defines a containing space 316, where a radius of the containing space 316 is greater than that of the first channel section 333.

The inner surrounding wall 32 is disposed in the containing space 316, and includes a second inner surface 321, a second outer surface 322, and a bearing surface 323. The second inner surface 321 surrounds the second channel section 334. The second outer surface 322 is opposite to the second inner surface 321 in the radial direction and is surrounded by the second surface portion 314. The flange 324 extends from the second outer surface 322 radially outward in the radial direction, and is adjacent to the second opening 332. Each of the second inner surface 321 and the second outer surface 322 has an edge opposite to the second opening 332 (i.e., a top edge in the axial direction (Z)). The bearing surface 323 has a ring shape having an outer circumference that is connected to the edge of the second outer surface 322 and an inner circumference that is connected to the edge of the second inner surface 321, and the bearing surface 323 faces the first openings 331, where the shouldering surface portion 315 of the first inner surface 311 is laid on the bearing surface 323.

The engaging mechanism 34 includes two bases 341 that are disposed on the second outer surface 322 of the inner surrounding wall 32, and two hooks 342 that extend, from an end of the outer surrounding wall 31 that is adjacent to the second opening 332, toward the second opening 332 (i.e., the hooks 342 extend downwardly from the bottom of the outer surrounding wall 31 in the axial direction (Z)), and that are connected to the bases 341 respectively. Specifically, each of the bases 341 is formed with an inner space, and the hooks 342 are inserted into the inner spaces respectively of the bases 341 such that the hooks 342 removably engage the bases 341.

Referring to FIGS. 3, 6, 7 and 15, the diaphragm 4 is disposed in the first channel section 333, and is formed with a through hole 45 that extends through the diaphragm 4 along the axial direction (Z) and that has a radius smaller than that of the second channel section 334. The diaphragm 4 includes a first surface 41 that faces the first openings 331, a second surface 42 that is opposite to the first surface 41 in the axial direction (Z) and that faces the second opening 332, an inner surrounding side 43 that defines the through hole 45, and an outer surrounding side 44 that is opposite to the inner surrounding side 43 in the radial direction.

The engaging unit 5 includes a first engaging part 51 that is formed on the first surface portion 313 of the first inner surface 311, and a second engaging part 52 that is formed on the diaphragm 4 and that movably engages the first engaging part 51. Specifically, the first engaging part 51 is formed on the first surface portion 313 at a position adjacent to the shouldering surface portion 315.

The first engaging part 51 has a restricting slot 511, a restricting surface 512, and an engaging space 513. The restricting slot 511 extends radially outward from the first surface portion 313 of the first inner surface 311 toward the first outer surface 312, and has a first side (bottom side) adjacent to the bearing surface 323 and a second side (top side) opposite to the first side in the axial direction (Z). The restricting surface 512 defines the second side of the restricting slot 511 and faces the bearing surface 323. The engaging space 513 extends from the restricting surface 512 in the axial direction (Z) away from the bearing surface 323 (i.e., the engaging space 513 extends upwardly from the restricting surface 512) and is in spatial communication with the restricting slot 511. To describe in further detail, the restricting surface 512 extends, from the first inner surface 311, radially outward in an inclined direction toward the second opening 332 (i.e., downwardly and radially outward).

The second engaging part 52 includes an extension part 521 that extends radially outward from the outer surrounding side 44 of the diaphragm 4 in the radial direction, and a bulge 522 that extends from the extension part 521 in the axial direction (Z) away from the bearing surface 323 (i.e., extends upwardly). The extension part 521 is disposed in the restricting slot 511, and the bulge 522 movably engages the engaging space 513.

The connection component 6 is adapted to connect the nasal plugs 2, and includes two rings 61 that respectively surround the nasal plugs 2, and a bridge 62 that is connected between the rings 61 and that has a curved shape.

Figure 7:
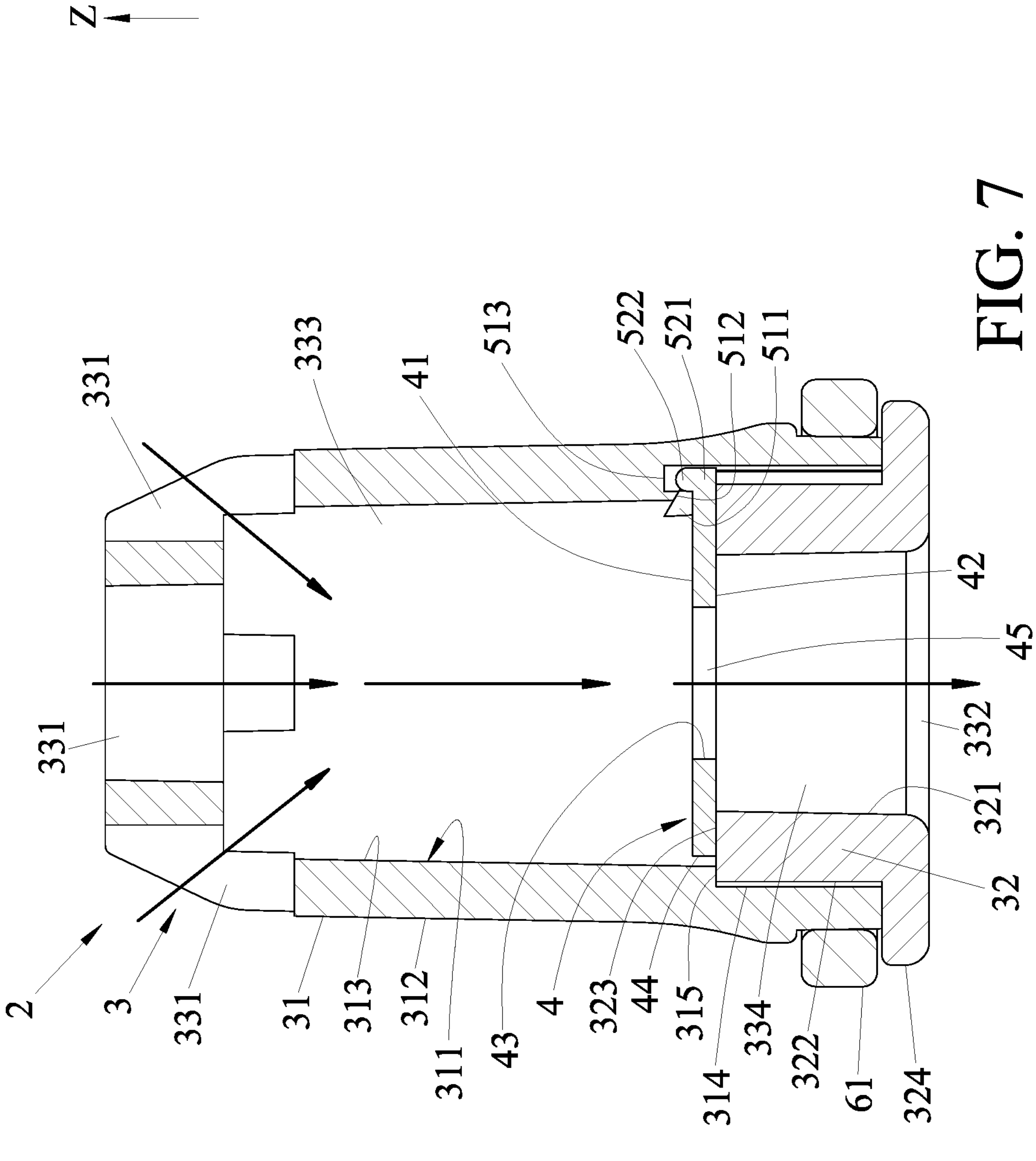
FIG. 7 is a sectional view taken along line VII-VII in FIG. 5, illustrating a diaphragm of the nasal plug being in an exhaling position according to the first embodiment of the disclosure.
Figure 8:
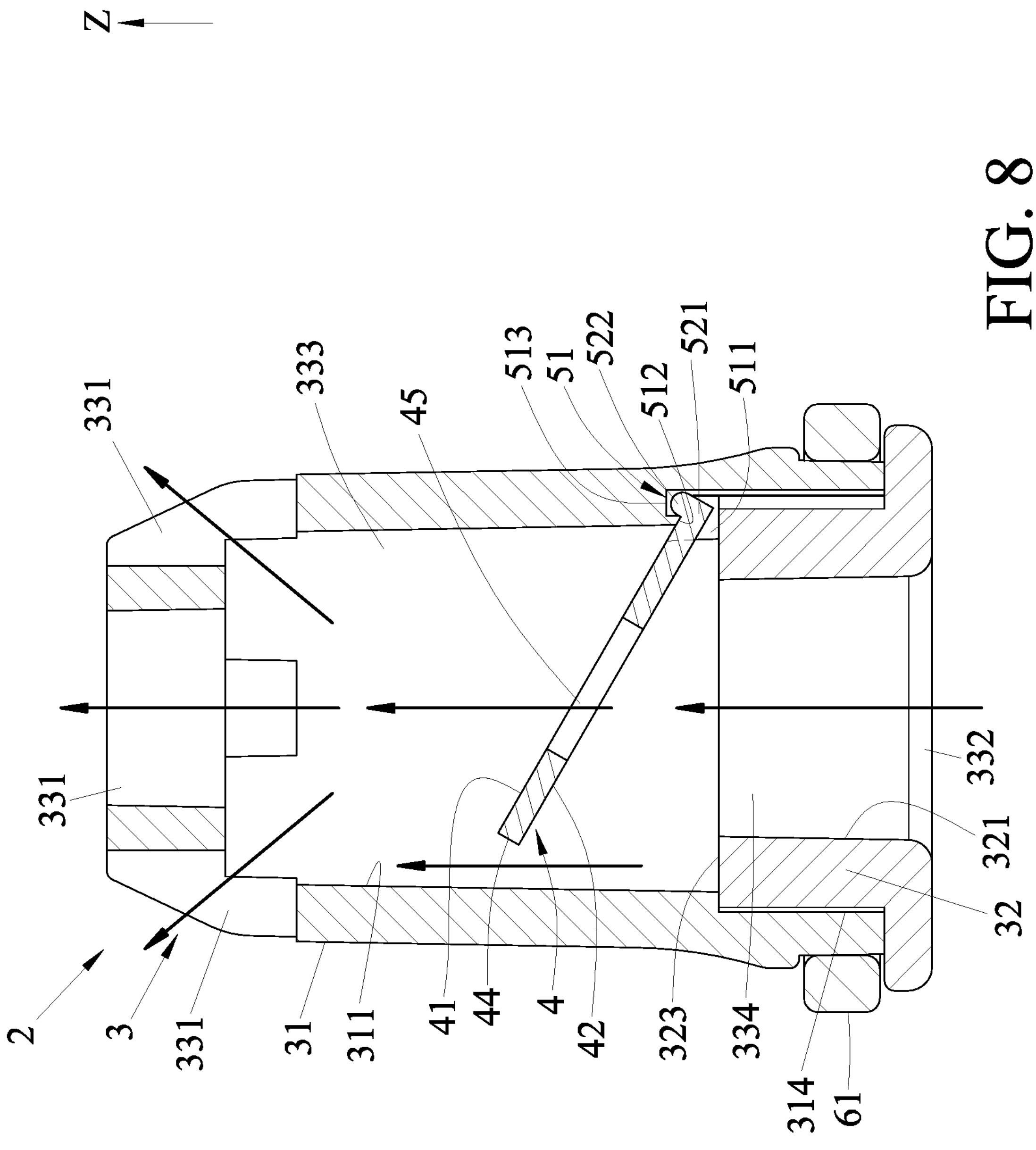
FIG. 8 is a sectional view similar to FIG. 7, illustrating the diaphragm in an inhaling position according to the first embodiment of the disclosure.
Figure 9:
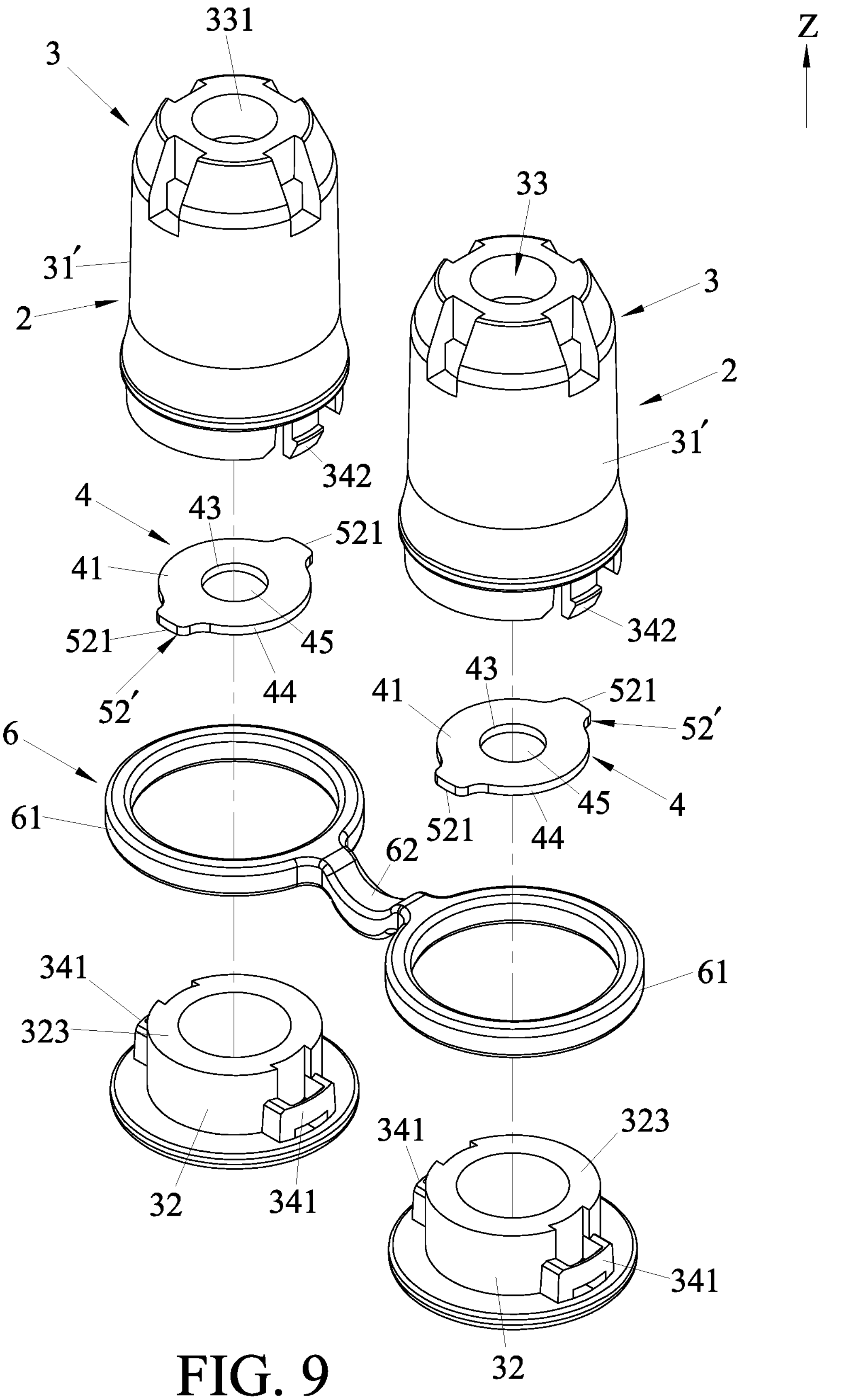
FIG. 9 is an exploded perspective view illustrating the diaphragm nasal breathing regulator according to a second embodiment of the disclosure.
Figure 10:
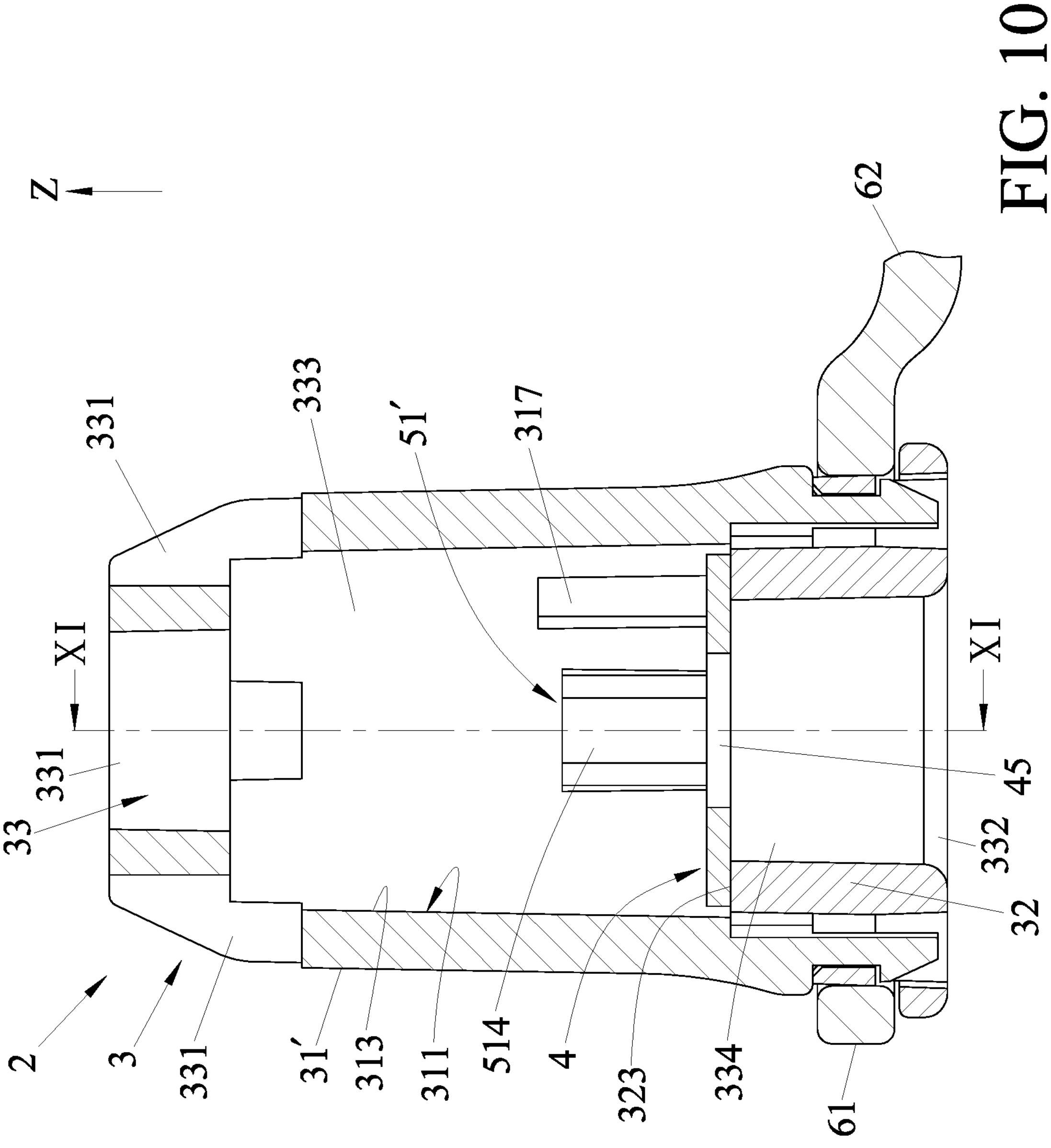
FIG. 10 is a fragmentary sectional view illustrating the nasal plug of the diaphragm nasal breathing regulator according to the second embodiment of the disclosure.

Further referring to FIG. 8, the bulge 522 movably engages the engaging space 513 in a manner where the diaphragm 4 is movable relative to the bearing surface 323 between an inhaling positon (see FIG. 8) and an exhaling position (see FIG. 7).

When a user (not shown) using the diaphragm nasal breathing regulator is inhaling, air flows from the second opening 332 into the second channel section 334 and impels the diaphragm 4 to move upwardly from the exhaling position to the inhaling position, which is away from the bearing surface 323 in the axial direction (Z). In this embodiment, when the diaphragm 4 is in the inhaling position, the extension part 521 is in contact with the restricting surface 512, and one end of the diaphragm 4 that is adjacent to the first engaging part 51 is closer to the second opening 332, in the axial direction (Z), than another end of the diaphragm 4 that is farther from the first engaging part 51. That is to say, when the diaphragm 4 is in the inhaling position, the diaphragm 4 is inclined relative to the bearing surface 323. In such as case, air can flow through the second opening 332, the second channel section 334, the through hole 45, the first channel section 333, a gap between the first inner surface 311 and the outer surrounding side 44, and the first openings 331.

When the user is exhaling, air flows from the first openings 331 into the first channel section 333 and impels the diaphragm 4 downwardly to the exhaling position. When the diaphragm 4 is in the exhaling position, the first surface 41 of the diaphragm 4 is away from the restriction surface 512 in the axial direction (Z), and the second surface 42 of the diaphragm 4 rests on the bearing surface 323. In such as case, air can flow only through the first openings 331, the first channel section 333, the through hole 45, the second channel section 334, and the second opening 332.

In comparison to the diaphragm 4 in the exhaling position, the diaphragm 4 in the inhaling position allows air to flow further through the gap between the first inner surface 311 of the outer surrounding wall 31 and the outer surrounding side 44 of the diaphragm 4. As such, an amount of airflow through the nasal plug 2 when the diaphragm 4 is in the inhaling position is greater than that of when the diaphragm 4 is in the exhaling position, thus ensuring smooth breathing and improving comfort of the user, and regulating the amount of airflow when the user is exhaling so as to reduce noises caused thereby.

It should be noted that, in the first embodiment, the connection component 6 is used for connecting the nasal plugs 2 to prevent any one of the nasal plugs 2 from being lost, but in some embodiments, the connection component 6 may be omitted. Furthermore, in the first embodiment, the two nasal plugs 2 are used to be respectively inserted into two nostrils of the user, but in some embodiments, only one nasal plug 2 may be used to be inserted into a nostril of the user according to user needs.

Referring to FIGS. 9 to 12, the diaphragm nasal breathing regulator according to a second embodiment of the disclosure is similar to the first embodiment. Differences between the two embodiments will be described in the following.

In the second embodiment, the first engaging part 51' only has two guiding slots 514 that are formed on the first surface portion 313 of the first inner surface 311, that are opposite to each other in the radial direction, and that extend from the bearing surface 323 toward the first openings 331 in the axial direction (Z) (i.e., extending upward from the bearing surface 323). The second engaging part 52' includes two of the extension parts 521, and the bulge 522 of the first embodiment is omitted. The extension parts 521 extend radially outward from the outer surrounding side 44 of the diaphragm 4 and movably engage the guiding slots 514 respectively.

In this embodiment, the outer surrounding wall 31' of the cylinder 3 further includes two air passages 317 that are on the first inner surface 311 of the outer surrounding wall 31' and that are opposite to each other in the radial direction, where the air passages 317 extend from the bearing surface 323 toward the first openings 331 in the axial direction (Z) (i.e., extend upward from the bearing surface 323).

In the second embodiment, there are two air passages 317, but in some embodiments, there may be only one air passage 317 or more than two air passages 317.

Figure 11:
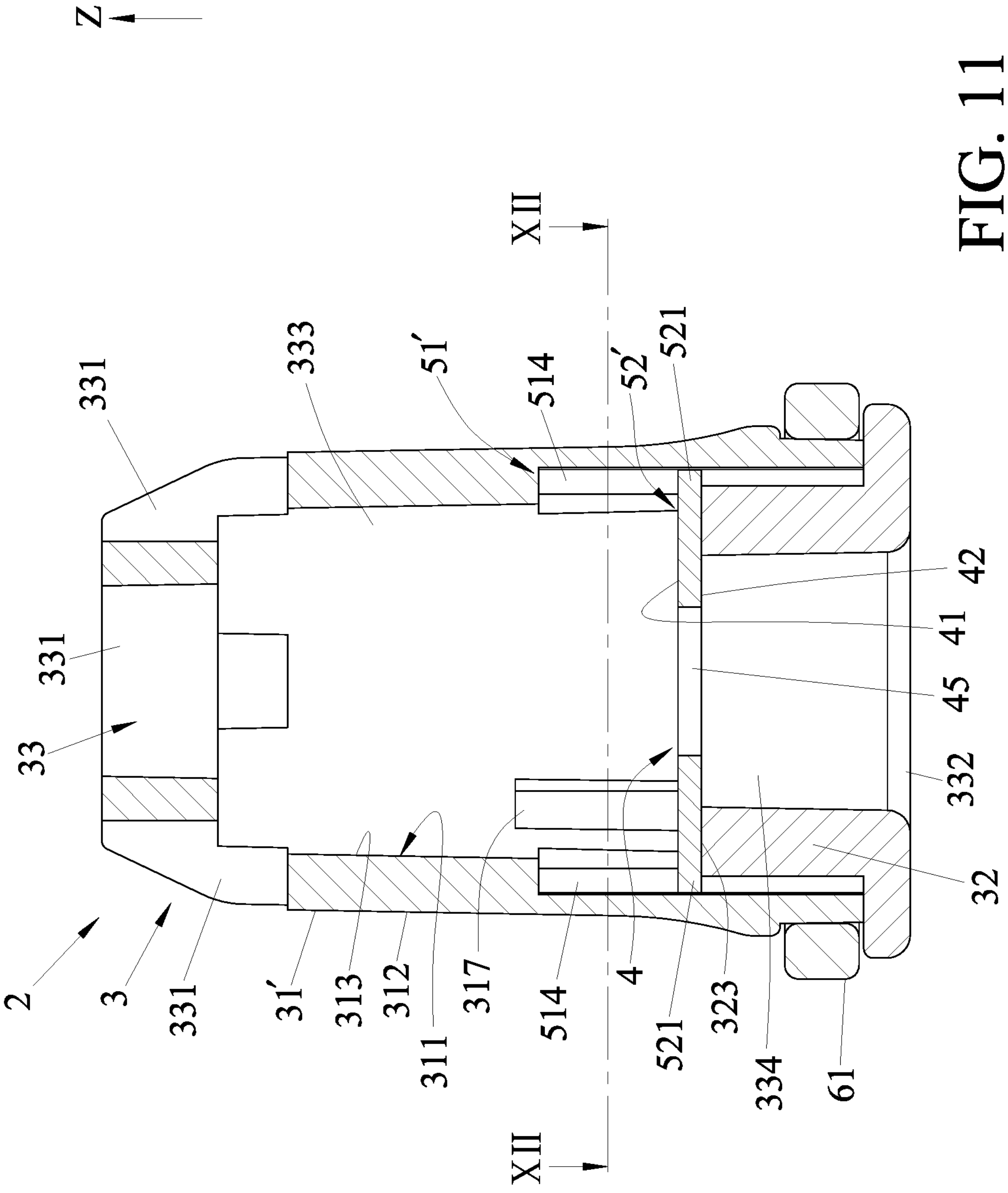
FIG. 11 is a sectional view taken along line XI-XI in FIG. 10, illustrating the diaphragm in the exhaling position according to the second embodiment of the disclosure.
Figure 12:
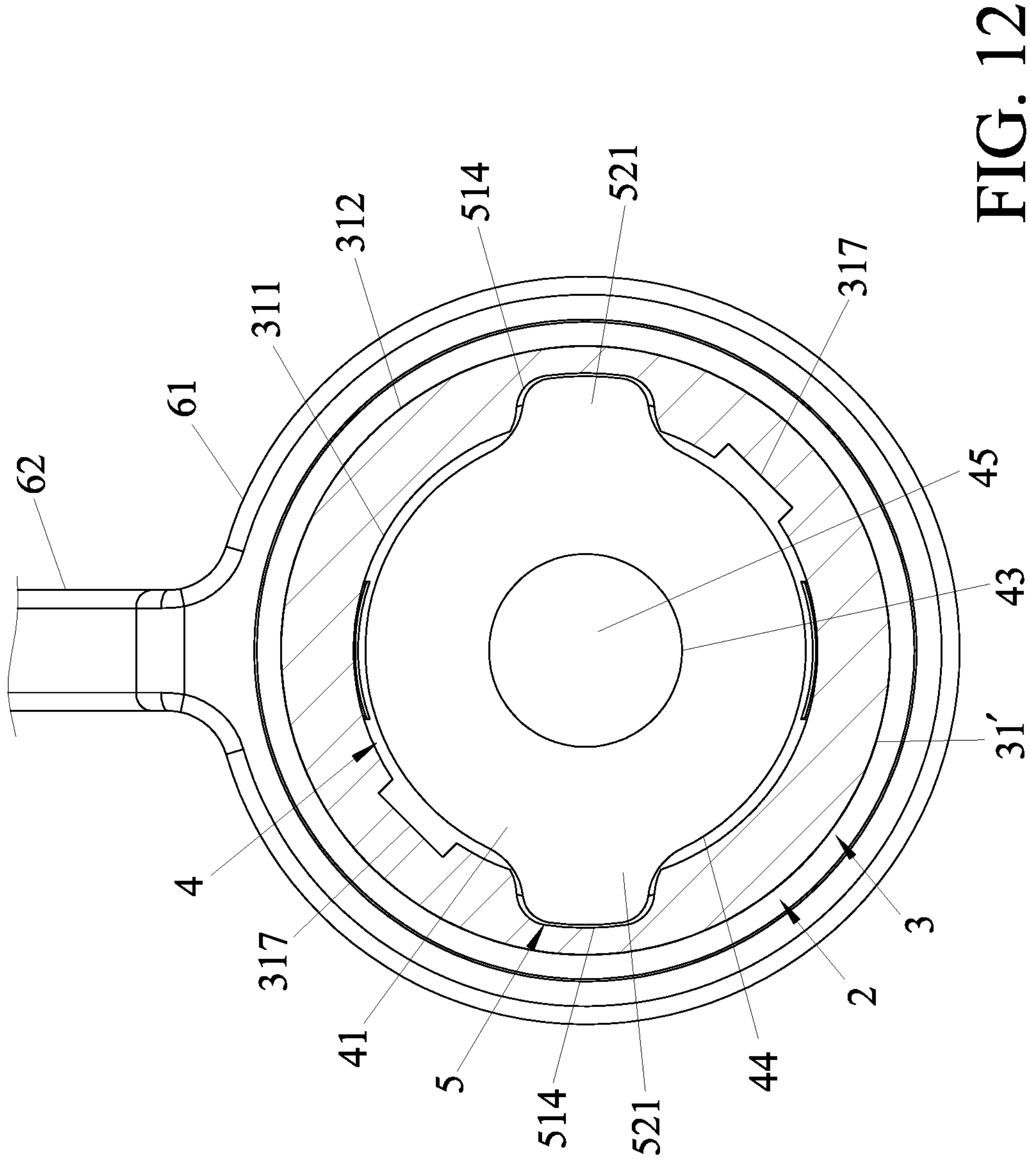
FIG. 12 is a cross-sectional view taken along line XII-XII in FIG. 11, illustrating the diaphragm nasal breathing regulator according to the second embodiment of the disclosure.
Figure 13:
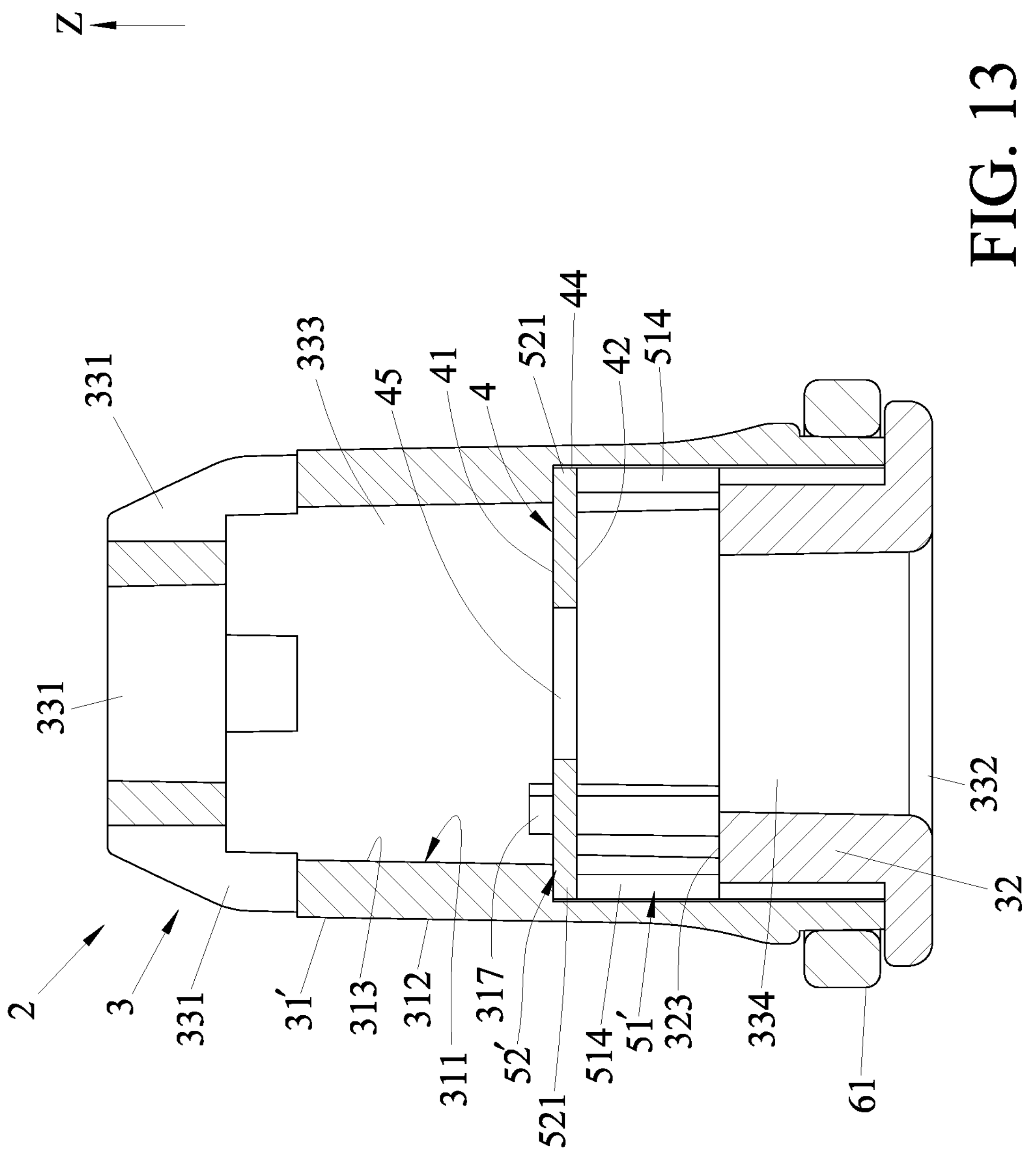
FIG. 13 is a sectional view similar to FIG. 11, illustrating the diaphragm in the inhaling position according to the second embodiment of the disclosure.

Referring to FIG. 11, when the diaphragm 4 is in the exhaling position, the second surface 42 of the diaphragm 4 rests on the bearing surface 323, and air can flow only through the first openings 331, the first channel section 333, the through hole 45, the second channel section 334, and the second opening 332. Referring to FIG. 13, when the diaphragm 4 is in the inhaling position, the second surface 42 of the diaphragm 4 is away from the bearing surface 323 in the axial direction (Z), and air can flow through the second opening 332, the second channel section 334, the through hole 45, the air passages 317 each between the outer surrounding side 44 and the first inner surface 311, the first channel section 333, and the first openings 331.

In the second embodiment, the diaphragm 4 is movable between the inhaling position (FIG. 13) and the exhaling position (FIG. 11) by the extension parts 521 moving up and down along the guiding slots 514, such that movement of the diaphragm 4 is stable.

Figure 14:
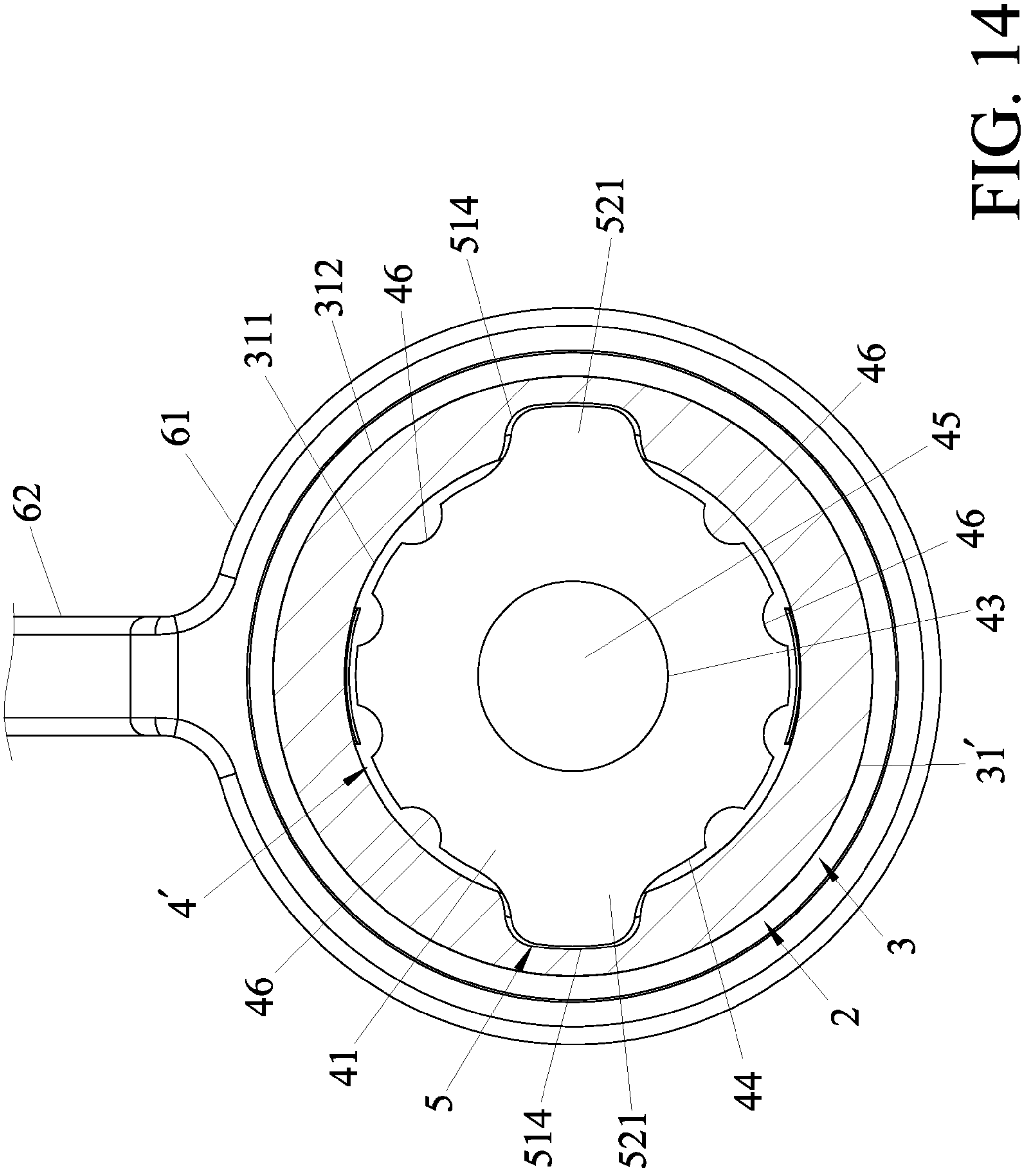
FIG. 14 is a cross-sectional view similar to FIG. 12, illustrating the diaphragm nasal breathing regulator according to a third embodiment of the disclosure.
Figure 15:
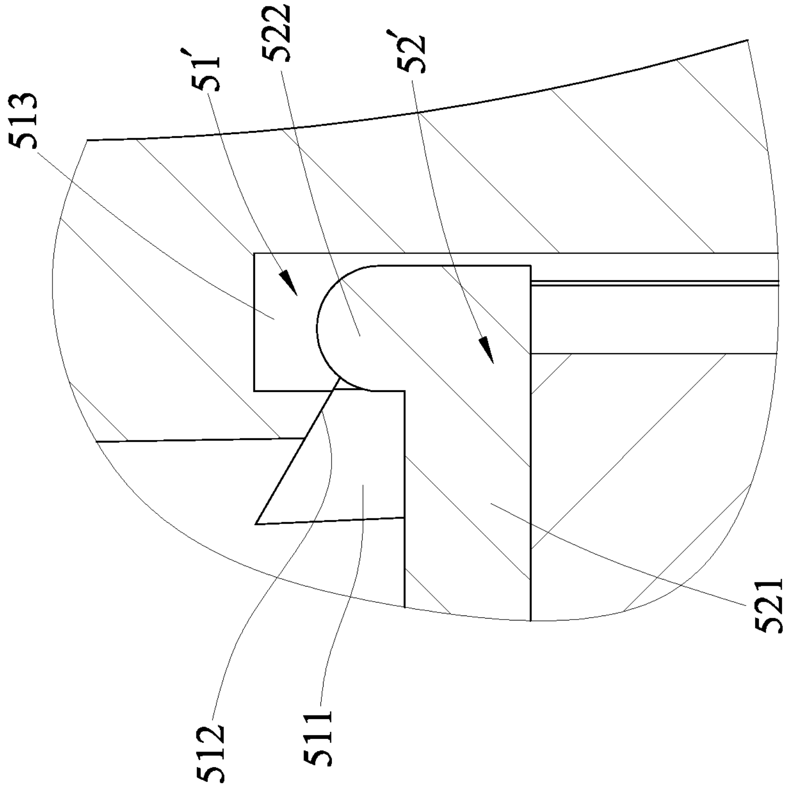
FIG. 15 is an enlarged sectional view illustrating a portion of the diaphragm nasal breathing regulator shown in FIG. 7.

Further referring to FIG. 14, the diaphragm nasal breathing regulator according to a third embodiment of the disclosure is similar to the second embodiment. Differences between the two embodiments will be described in the following.

In the third embodiment, the diaphragm 4' is formed with a plurality of air slots 46 that extend radially inward from the outer surrounding side 44 toward the inner surrounding side 43, and the outer surrounding wall 31' omits the air passages 317. However, in some embodiments, the outer surrounding wall 31' may have the air passages 317 while the diaphragm 4' has the air slots 46. In this embodiment, there are eight air slots 46, but in some embodiments, there may be, but not limited to, only one air slot 46.

When the diaphragm 4' is in the inhaling position, air can flow through the second opening 332, the second channel section 334, the through hole 45, the air slots 46 each between the outer surrounding side 44 and the first inner surface 311, the first channel section 333, and the first openings 331. As such, the third embodiment provides substantially the same function as the second embodiment.

In summary, the diaphragm 4, 4' of the disclosure is able to be moved between the inhaling position and the exhaling position. When the diaphragm 4, 4' is in the exhaling position, the diaphragm 4, 4' rests on the bearing surface 323. When the diaphragm 4, 4' is in the inhaling position, the diaphragm 4, 4' is away from the bearing surface 323 in the axial direction (Z) so that air can flow through the gap between the first inner surface 311 and the outer surrounding side 44, the air passages 317, or the air slots 46. As such, the amount of airflow through the nasal plugs 2 when the diaphragm 4, 4' is in the inhaling position is greater than that of when the diaphragm 4, 4' is in the exhaling position, thus ensuring smooth breathing and improving comfort of the user, and regulating the amount of airflow when the user is breathing.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects; such does not mean that every one of these features needs to be practiced with the presence of all the other features. In other words, in any described embodiment, when implementation of one or more features or specific details does not affect implementation of another one or more features or specific details, said one or more features may be singled out and practiced alone without said another one or more features or specific details. It should be further noted that one or more features or specific details from one embodiment may be practiced together with one or more features or specific details from another embodiment, where appropriate, in the practice of the disclosure.

While the disclosure has been described in connection with what is(are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A diaphragm nasal breathing regulator comprising a nasal plug that includes:

a cylinder surrounding and defining a channel that extends in an axial direction of said cylinder, that has a first opening and a second opening opposite to each other along the axial direction, and that includes a first channel section adjacent to said first opening and a second channel section adjacent to said second opening, where a radius of said second channel section is smaller than that of said first channel section, said cylinder including a first inner surface that surrounds and defines said first channel section, a second inner surface that surrounds and defines said second channel section and that has an edge opposite to said second opening, and a bearing surface that is connected to said edge of said second inner surface and that faces said first opening;

a diaphragm disposed in said first channel section and formed with a through hole that extends through said diaphragm along the axial direction and that has a radius smaller than that of said second channel section, said diaphragm including a first surface and a second surface that are opposite to each other along the axial direction and that face said first opening and said second opening respectively, an inner surrounding side that defines said through hole, and an outer surrounding side that is opposite to said inner surrounding side in a radial direction perpendicular to the axial direction; and an engaging unit including a first engaging part that is formed on said first inner surface, and a second engaging part that is formed on said diaphragm and that movably engages said first engaging part in a manner where said diaphragm is movable relative to said bearing surface between an inhaling positon and an exhaling position;

wherein, when said diaphragm is in the exhaling position, said second surface of said diaphragm rests on said bearing surface, and air can flow only through said first opening, said first channel section, said through hole, said second channel section, and said second opening, and wherein, when said diaphragm is in the inhaling position, said diaphragm is away from said bearing surface in the axial direction, and air can flow through said second opening, said second channel section, said through hole, said first channel section, a gap between said first inner surface and said outer surrounding side, and said first opening.

2. The diaphragm nasal breathing regulator as claimed in claim 1, wherein:

said first engaging part has a restricting slot that extends radially outward from said first inner surface and that has a first side adjacent to said bearing surface and a second side opposite to said first side in the axial direction, a restricting surface that defines said second side of said restricting slot and that faces said bearing surface, and an engaging space that extends from said restricting surface in the axial direction away from said bearing surface and that is in spatial communication with said restricting slot;

said second engaging part includes an extension part that extends radially outward from said outer surrounding side of said diaphragm and that is disposed in said restricting slot, and a bulge that extends from said extension part in the axial direction away from said bearing surface and that movably engages said engaging space;

when said diaphragm is in the exhaling position, said first surface of said diaphragm is away from said restricting surface in the axial direction; and when said diaphragm is in the inhaling position, said extension part is in contact with said restricting surface.

3. The diaphragm nasal breathing regulator as claimed in claim 2, wherein:

said restricting surface extends, from said first inner surface, radially outward in an inclined direction toward said second opening; and when said diaphragm is in the inhaling position, one end of said diaphragm that is adjacent to said first engaging part is closer to said second opening, in the axial direction, than another end of said diaphragm that is farther from said first engaging part.

4. The diaphragm nasal breathing regulator as claimed in claim 1, wherein:

said first engaging part has two guiding slots that are formed on said first inner surface, that are opposite to each other in the radial direction, and that extend from said bearing surface toward said first opening in the axial direction; and said second engaging part includes two extension parts that extend radially outward from said outer surrounding side of said diaphragm and that movably engage said guiding slots respectively.

5. The diaphragm nasal breathing regulator as claimed in claim 4, wherein said cylinder is formed with an air passage on said first inner surface, said air passage extending from said bearing surface toward said first opening in the axial direction.

6. The diaphragm nasal breathing regulator as claimed in claim 4, wherein said diaphragm is formed with an air slot that extends radially inward from said outer surrounding side toward said inner surrounding side.

7. The diaphragm nasal breathing regulator as claimed in claim 1, wherein said cylinder is formed with an air passage on said first inner surface, said air passage extending from said bearing surface toward said first opening in the axial direction.

8. The diaphragm nasal breathing regulator as claimed in claim 1, wherein said diaphragm is formed with an air slot that extends radially inward from said outer surrounding side toward said inner surrounding side.

9. The diaphragm nasal breathing regulator as claimed in claim 1, wherein:

said cylinder includes an outer surrounding wall, an inner surrounding wall that is surrounded by said outer surrounding wall and that is detachably connected to said outer surrounding wall, and an engaging mechanism that interconnects said outer surrounding wall and said inner surrounding wall;

said outer surrounding wall and said inner surrounding wall cooperatively surround and define said channel;

said outer surrounding wall includes said first inner surface, and said first inner surface includes a first surface portion that is adjacent to said first opening and that surrounds said first channel section, and a second surface portion that is adjacent to said second opening and that surrounds and defines a containing space; and said inner surrounding wall is disposed in said containing space, and includes said second inner surface, said bearing surface, and an outer surface that is opposite to said second inner surface in the radial direction and that is surrounded by said second surface portion, where said outer surface has an edge opposite to said second opening, and said bearing surface has a ring shape having an outer circumference connected to said edge of said outer surface and an inner circumference connected to said edge of said second inner surface.

10. The diaphragm nasal breathing regulator as claimed in claim 9, wherein said engaging mechanism includes a plurality of bases that are disposed on said inner surrounding wall, and a plurality of hooks that extend, from an end of said outer surrounding wall adjacent to said second opening, toward said second opening, and that are connected to said bases respectively.

11. The diaphragm nasal breathing regulator as claimed in claim 9, wherein a radius of said containing space is greater than that of said first channel section, and said first inner surface further includes a shouldering surface portion that is connected to and between said first surface portion and said second surface portion, and that is laid on said bearing surface of said inner surrounding wall.

12. The diaphragm nasal breathing regulator as claimed in claim 1, comprising:

two of said nasal plugs; and a connection component that is adapted to connect said nasal plugs, and that includes two rings respectively surrounding said nasal plugs, and a bridge connected between said rings.

* * * * *